United States Patent
Kraemer et al.

(10) Patent No.: US 7,498,379 B2
(45) Date of Patent: Mar. 3, 2009

(54) CARBODIIMIDES CONTAINING UREA GROUPS AND SILYL-GROUPS

(75) Inventors: Markus Kraemer, Stemshorn (DE); Oliver Steffen Henze, Schneidlingen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 54 days.

(21) Appl. No.: 11/568,808

(22) PCT Filed: May 6, 2005

(86) PCT No.: PCT/EP2005/004917
§ 371 (c)(1), (2), (4) Date: Nov. 8, 2006

(87) PCT Pub. No.: WO2005/111048
PCT Pub. Date: Nov. 24, 2005

(65) Prior Publication Data
US 2008/0015294 A1    Jan. 17, 2008

(30) Foreign Application Priority Data
May 13, 2004    (DE)    ........................ 10 2004 024 196

(51) Int. Cl.
C08K 5/5419    (2006.01)
C07F 7/10    (2006.01)

(52) U.S. Cl. ...................... 524/588; 556/421
(58) Field of Classification Search ................. 524/188; 556/421
See application file for complete search history.

(56) References Cited

U.S. PATENT DOCUMENTS

| | | | | |
|---|---|---|---|---|
| 4,118,536 A * | 10/1978 | Beardsley et al. | ........... | 428/413 |
| 4,977,219 A * | 12/1990 | Watson, Jr. | ............... | 525/329.5 |
| 5,008,363 A * | 4/1991 | Mallon et al. | .................. | 528/49 |
| 5,357,021 A * | 10/1994 | Tye et al. | ....................... | 528/28 |
| 5,578,675 A * | 11/1996 | Mormile et al. | ............. | 524/589 |
| 6,329,491 B1 * | 12/2001 | Mormile et al. | ............... | 528/49 |
| 2003/0027921 A1 * | 2/2003 | Speier et al. | ................. | 524/589 |
| 2004/0138396 A1 * | 7/2004 | Gabriel | ......................... | 528/17 |
| 2004/0244829 A1 * | 12/2004 | Rearick et al. | .............. | 136/251 |

FOREIGN PATENT DOCUMENTS

| | | |
|---|---|---|
| DE | 43 18 979 | 12/1994 |
| DE | 44 42 724 | 6/1996 |
| EP | 0 460 481 | 12/1991 |
| EP | 0 507 407 | 10/1992 |
| EP | 0 628 541 | 12/1994 |
| EP | 0 785 222 | 7/1997 |
| EP | 0 969 029 | 1/2000 |
| EP | 1 162 237 | 12/2001 |

* cited by examiner

*Primary Examiner*—Randy Gulakowski
*Assistant Examiner*—Robert Loewe
(74) *Attorney, Agent, or Firm*—Oblon, Spivak, McClelland, Maier & Neustadt, P.C.

(57) ABSTRACT

Carbodiimide containing at least one silane group bonded by way of urea groups.

Carbodiimide containing the following structure:

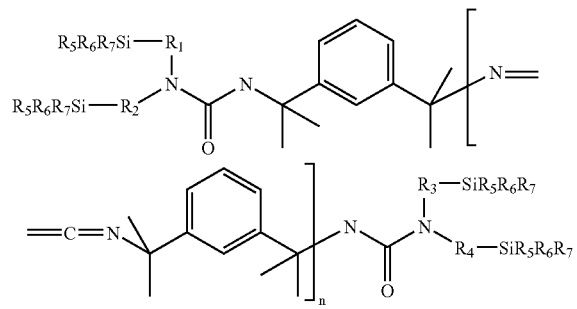

with the following meanings for n, $R_1$, $R_2$, $R_3$, $R_4$, $R_5$, $R_6$ and $R_7$:

n: 1, 2, 3, 4, 5, 6, 7, 8, 9, 10, 11, 12, 13, 14, 15, 16, 17, 18, 19, or 20, $R_1$: aliphatic, cycloaliphatic, araliphatic, or aromatic, if appropriate substituted, if appropriate branched-chain radical, $R_2$: aliphatic, cycloaliphatic, araliphatic, or aromatic, if appropriate substituted, if appropriate branched-chain radical, $R_3$: aliphatic, cycloaliphatic, araliphatic, or aromatic, if appropriate substituted, if appropriate branched-chain radical, $R_4$: aliphatic, cycloaliphatic, araliphatic, or aromatic, if appropriate substituted, if appropriate branched-chain radical, $R_5$: methyl-, ethyl, $-O-CH_3$, $-O-CH_2-CH_3$, $-O-CH(CH_3)_2$, $-O-C(CH_3)_3$, or $-O-CH_2-CH_2-O-CH_3$ $R_6$: methyl-, ethyl, $-O-CH_3$, $-O-CH_2-CH_3$, $-O-CH(CH_3)_2$, $-O-C(CH_3)_3$, or $-O-CH_2-CH_2-O-CH_3$ $R_7$: methyl-, ethyl, $-O-CH_3$, $-O-CH_2-CH_3$, $-O-CH(CH_3)_2$, $-O-C(CH_3)_3$, or $-O-CH_2-CH_2-O-CH_3$.

10 Claims, No Drawings

CARBODIIMIDES CONTAINING UREA GROUPS AND SILYL-GROUPS

The invention relates to carbodiimides containing at least one, preferably from 2 to 6, particularly preferably 4, silane groups bonded by way of a urea group, and also to processes for preparing these carbodiimides. The invention further relates to mixtures comprising the inventive carbodiimides and at least one compound from the following group: polyurethanes which have ester structures, polyethylene terephthalate and/or polybutylene terephthalate, polyetheresters, polyesteramides, polycaprolactones, unsaturated polyester resins, polyamides, in particular thermoplastic polyurethanes comprising the inventive carbodiimides and preferably containing ester structures. The expression "silane groups" in this specification particularly means organosilicon groups.

Organic carbodiimides are known and are used by way of example as stabilizer to inhibit hydrolytic degradation of compounds containing ester groups, for example of polyaddition and polycondensation products, e.g. polyurethanes. Carbodiimides can be prepared by well-known processes, e.g. via action of basic catalysts on mono- or polyisocyanates with elimination of carbon dioxide. Examples of suitable catalysts are heterocyclic phosphorus-containing compounds, metal carbonyls, phospholines, phospholenes, and phospholidines, and also their oxides and sulfides.

By way of example, DE-A 4 318 979, DE-A 4 442 724, and EP-A 460 481 describe these carbodiimides, their preparation, and their use as stabilizers to inhibit hydrolytic cleavage of polyester-based plastics.

The prior art also discloses that carbodiimides can be modified with alkoxysilanes. EP-A 969 029, EP-A 785 222, EP-A 507 407, EP-A 1 162 237, and U.S. Pat. No. 4,118,536 describe the preparation of carbodiimides which have alkoxysilane end groups, for example.

The object of the present invention was to develop improved carbodiimides which are stabilizers to inhibit hydrolytic cleavage of polyester-based plastics, which have ideal ease of incorporation into the starting components of the plastics or into the plastics themselves, and which moreover do not adversely affect the dynamic and static properties of the plastics, in particular of polyurethane elastomers. A particular objective was to retain the property profile of the plastics to be stabilized, in particular of the thermoplastic polyurethane, even under conditions in which hydrolysis usually occurs.

This object has been achieved by the carbodiimides described at the outset.

In purely statistical terms, the hydrolytic degradation of a polyester cleaves one molecule to give two molecules. This is associated with a corresponding fall in molar mass. When the carbodiimide is used, the acid-containing polymer radical is intercepted, the result being combination of these two molecules. However, this does not solve the problem of molecular weight degradation. The particular advantage of the inventive carbodiimides is firstly their excellent efficacy as hydrolysis stabilizers and secondly their ability, by way of the siloxane groups at the end of the carbodiimide, to generate crosslinking and thus increase the molar masses within the polymer. This particular advantage is especially useful in thermoplastics, being particularly advantageous in thermoplastic polyurethane.

The inventive carbodiimides provide, via the linkage of preferably 4 silane groups by way of the urea group to the carbodiimide, particularly good crosslinking capacity which can bring about a marked increase in molecular weight in the polymer, thus giving the polymer very good properties.

Other advantages of the inventive carbodiimides are the following:
  easy to prepare
  can be incorporated into TPU without side-reactions
  low viscosities at processing temperature (60° C.)
  pumpable at room temperature
  stable in storage
  effective as hydrolysis stabilizers, in particular when catalyst is absent, i.e. with markedly reduced content of, by way of example, phospholene oxide
  low volatility
  low cost
  reaction in bulk, i.e. without solvent The TPUs prepared using the inventive carbodiimides have the following advantages, when comparison is made with conventional carbodiimides:
  improved resistance to hydrolysis during aging in water at 80° C.
  improvement (increase) in tensile strength and tensile strain at break during underwater aging
  crosslinking of the siloxane groups in situ during use in the presence of moisture, i.e. no additional crosslinking operation
  reduced level of swelling properties
  increased heat resistance
  increased HDT
  increased modulus of elasticity
  increased Vicat point The following carbodiimides are preferred:

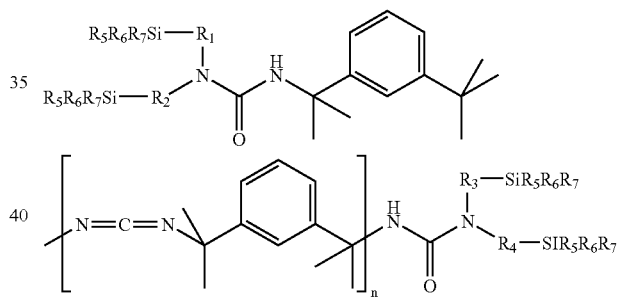

with the following meanings for n, $R_1$, $R_2$, $R_3$, $R_4$, $R_5$, $R_6$ and $R_7$:

n: 1, 2, 3, 4, 5, 6, 7, 8, 9, 10, 11, 12, 13, 14, 15, 16, 17, 18, 19, or 20, preferably from 2 to 15, particularly preferably from 3 to 10, $R_1$: aliphatic, cycloaliphatic, araliphatic, or aromatic, if appropriate substituted, if appropriate branched-chain radical, preferably an alkylene radical having from 1 to 20, preferably from 2 to 10, particularly preferably from 2 to 4, carbon atoms, $R_2$: aliphatic, cycloaliphatic, araliphatic, or aromatic, if appropriate substituted, if appropriate branched-chain radical, preferably an alkylene radical having from 1 to 20, preferably from 2 to 10, particularly preferably from 2 to 4, carbon atoms, $R_3$: aliphatic, cycloaliphatic, araliphatic, or aromatic, if appropriate substituted, if appropriate branched-chain radical, preferably an alkylene radical having from 1 to 20, preferably from 2 to 10, particularly preferably from 2 to 4, carbon atoms, $R_4$: aliphatic, cycloaliphatic, araliphatic, or aromatic, if appropriate substituted, if appropriate branched-chain radical, preferably an alkylene radical having from 1 to 20, preferably from 2 to 10, particularly preferably from 2 to 4, carbon atoms, $R_5$: methyl-, ethyl, —O—CH$_3$, —O—CH$_2$—CH$_3$, —O—CH(CH$_3$)$_2$, or —O—C(CH$_3$)$_3$, —O—CH$_2$—CH$_2$—O—CH$_3$, preferably —O—CH$_3$ or —O—CH$_2$—CH$_3$, particularly preferably —O—CH$_3$, $R_6$: methyl-, ethyl, —O—CH$_3$, —O—CH$_2$—CH$_3$, —O—CH(CH$_3$)$_2$, or —O—C(CH$_3$)$_3$, —O—CH$_2$—CH$_2$—O—CH$_3$, preferably —O—CH$_3$ or —O—CH$_2$—CH$_3$, particularly preferably —O—CH$_3$, $R_7$: methyl-, ethyl, —O—CH$_3$, —O—CH$_2$—CH$_3$, —O—CH(CH$_3$)$_2$, or —O—C(CH$_3$)$_3$, —O—CH$_2$—CH$_2$—O—CH$_3$, preferably —O—CH$_3$ or —O—CH$_2$—CH$_3$, particularly preferably —O—CH$_3$.

The following carbodiimide is particularly preferred:

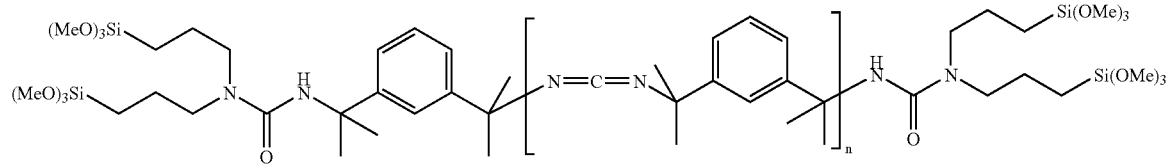

with the following meaning for n: 1, 2, 3, 4, 5, 6, 7, 8, 9, 10, 11, 12, 13, 14, 15, 16, 17, 18, 19 or 20, preferably from 2 to 15, particularly preferably from 3 to 10.

In essence, the preparation of the inventive carbodiimides takes place via two reactive steps. Firstly, carbodiimide structures are produced (1) via well-known reaction of the isocyanate groups with one another with elimination of carbon dioxide in the presence of conventional catalysts known for this reaction and described at the outset, and secondly isocyanate groups are reacted (2) with secondary amines which have at least one, preferably two, silane groups, to give urea structures. The sequence of these two substantive steps (1) and (2) in the process is as desired, as long as free isocyanate groups are present for each reaction.

By way of example, in one method of obtaining the inventive carbodiimides 1,3-bis(1-methyl-1-isocyanatoethyl)benzene is reacted in the presence of catalysts with elimination of carbon dioxide to give carbodiimides, and then the carbodiimide having isocyanate groups is reacted with a secondary amine containing at least one, preferably two, silane groups, preferably trialkoxysilane groups. The molar ratio of the NCO groups of the carbodiimide having isocyanate groups to those groups of the secondary amine that are reactive toward the isocyanates, in particular the secondary amino groups, is usually from 10:1 to 0.2:1, preferably from 5:1 to 0.5:1, particularly preferably from 1:1 to 0.5:1, in particular 1:1.

As an alternative, in another method of obtaining the inventive carbodiimides 1,3-bis(1-methyl-1-isocyanatoethyl)benzene is reacted with a submolar amount of secondary amine containing at least one, preferably two, silane groups, preferably trialkoxysilane groups, and then the reaction product having isocyanate groups is reacted in the presence of catalysts with release of carbon dioxide to give carbodiimides.

In this version of the process, up to 50% by weight, preferably up to 23% by weight, of the isocyanate groups of the diisocyanate are first reacted with the secondary amine, and then all or some of the free isocyanate groups are condensed in the presence of catalysts with liberation of carbon dioxide to give carbodiimides and/or oligomeric polycarbodiimides.

It is preferable for the reaction to give the carbodiimides to be carried out first and to be followed by the reaction of the carbodiimide having isocyanate groups with the secondary amine.

The product, i.e. the inventive carbodiimide, preferably has an NCO content smaller than 1.0% by weight, particularly preferably from 0.5 to 0.01% by weight.

Step (I) of the process for the preparation of the inventive carbodiimides via reaction of diisocyanates may be condensed at elevated temperatures, e.g. at temperatures of from 50 to 200° C., preferably from 150 to 185° C., advantageously in the presence of catalysts, with elimination of carbon dioxide. GB-A-1 083 410, DE-B 1 130 594 (GB-A-851 936), and DE-A-11 56 401 (U.S. Pat. No. 3,502,722) describe, by way of example, processes suitable for this purpose. Catalysts which have proven preferably suitable are, by way of example, phosphorus compounds, preferably selected from the group of the phospholenes, phospholene oxides, phospholidines, and phospholine oxides. Formation of the polycarbodiimide is usually terminated when the reaction mixture has the desired content of NCO groups. To this end, the catalysts may be distilled off at reduced pressure or deactivated via addition of a deactivator, e.g. phosphorus trichloride. According to the invention, preference is given to carbodiumides whose content of catalysts for carbodiimide formation is smaller than 5.0 ppm. The polycarbodiimides may moreover be prepared in the absence or presence of solvents inert under the reaction conditions.

The person skilled in the art can adjust the degree of condensation in the usual way via suitable choice of the reaction conditions, e.g. the reaction temperature, the type of catalyst, and the amount of catalyst, and also the reaction time. The simplest method of monitoring the reaction is determination of NCO content. Other parameters such as viscosity rise, deepening of color, or CO$_2$ evolution, can be utilized in order to monitor and control the reaction.

The isocyanate used to prepare the inventive carbodiimides may comprise well-known isocyanates, preferably diisocyanates. It is preferable to use 1,3-bis(1-methyl-1-isocyanatoethyl)benzene, hereinafter also termed TMXDI. TMXDI may be used in mixtures with other well-known isocyanates, such as hexamethylene diisocyanate, 1-isocyanato-3,3,5-trimethyl-5-isocyanatomethylcyclohexane (isophorone diisocyanate), di(cyclohexyl)methane diisocyanate, trimethylhexamethylene diisocyanate, dodecane diisocyanate, octane diisocyanate, and/or cyclohexane 1,4-diisocyanate. In this case, it is preferable to make concomitant use of at least 30 mol % of TMXDI.

The inventive carbodiimides containing at least one, preferably from one to twenty, carbodiimide structures, the average degree of condensation (number-average), i.e. the average number of carbodiimide structures in the inventive carbodiimides, is particularly preferably from 1 to 10, particularly preferably from 2 to 8, in particular from 4 to 6.

For the reaction with the isocyanate groups, and for the introduction of the silane groups bonded by way of urea groups, use may be made of well-known secondary amines having silane groups, and preferably having, besides the secondary amino groups, no other groups reactive toward isocyanates, in particular hydroxy and/or primary amino groups. The following compound is preferably used for the reaction with the isocyanates, and is obtainable from Osi Specialties:

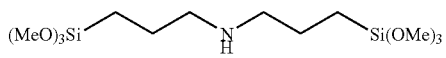

The inventive monocarbodiimides and/or oligomeric polycarbodiimides have excellent suitability as acceptors for carboxy compounds and are therefore preferably used as stabilizers to inhibit hydrolytic degradation of compounds containing ester groups, e.g. polymers containing ester groups, for example polycondensation products, such as thermoplastic polyesters, e.g. polyethylene terephthalate and polybutylene terephthalate, polyetheresters, polyamides, polyesteramides, polycaprolactones, and also unsaturated polyester resins, and polyesteresters, for example block copolymers composed of polyethylene terephthalate or of polybutylene terephthalate and polycaprolactone. And polyaddition products, e.g. polyurethanes, polyureas, and polyurethane-polyurea elastomers, containing ester groups. These compounds containing ester groups are well known. The standard literature has many descriptions of their starting materials, preparation processes, structures, and properties. The good solubility of the inventive (poly)carbodiimides in the structural components for the preparation of polyurethanes, and their good compatibility with the polyurethanes formed, make them particularly suitable as stabilizers to inhibit hydrolytic degradation of polyurethanes, preferably of compact or cellular polyurethane elastomers, and in particular of thermoplastic polyurethanes, and also of cellular or compact elastomers.

The concentration of the inventive carbodiimides in the polycondensation or poly-addition products to be stabilized and containing ester groups is generally from 0.05 to 10% by weight, preferably from 0.1 to 5% by weight, based on the total weight of the mixture. The concentration may also be higher in individual instances, depending on the level of hydrolytic stress to which the plastic is exposed.

Various methods can be used to introduce the carbodiimides which may be used according to the invention into the products which are to be stabilized and which contain ester groups. By way of example, the inventive carbodiimides may be mixed with one of the structural components for the preparation of the polyaddition products, e.g. with the polyisocyanates and/or polyhydroxy compounds for the preparation of polyurethanes, or the carbodiimides may be metered into the reaction mixture for the preparation of the polyurethanes. In another procedure, the inventive carbodiimides may be incorporated into the melt of the fully reacted polyaddition or polycondensation products. However, it is also possible for granules of the polyaddition or polycondensation products to be coated with the inventive carbodiimides, or mixed with the pulverized, pelletized, or granulated inventive carbodiimides, and introduced into the plastics compositions during subsequent production of moldings via melt extrusion. In one preferred embodiment for the preparation of pourable polyurethane elastomers and polyester-based TPUs, the polyester polyols containing carboxy groups are first treated with the inventive carbodiimides, to reduce acid content, and these are then reacted with polyisocyanates, if appropriate with addition of further amounts of carbodiimides, and if appropriate in the presence of additional auxiliaries and additives. The inventive carbodiimides may also be introduced into the polyurethane by way of the isocyanate component. However, the inventive carbodiimides are particularly useful when they are introduced into the polymer containing ester groups during conventional manufacturing processes.

The inventive carbodiimides are particularly preferably used during the preparation of polyurethanes, e.g. of cellular, for example microcellular, polyurethanes, preferably of polyurethane elastomers, in particular of thermoplastic polyurethanes. These polyurethanes, in particular polyurethane elastomers, may be prepared via known reaction of conventional starting components, i.e. isocyanates, compounds reactive toward isocyanates, if appropriate blowing agents, preferably water, and, if appropriate, catalysts, and auxiliaries and/or additives, in the presence of the inventive carbodiimides. Here, it is preferable for the inventive carbodiimides to be added to the component which comprises the blowing agent, preferably water.

Preference is therefore given to processes for the preparation of polyurethanes, preferably of thermoplastic polyurethanes, preferably via reaction of isocyanates, compounds reactive toward isocyanates, if appropriate blowing agents, and, if appropriate, catalysts, and auxiliaries and/or additives, where the reaction is carried out in the presence of the inventive carbodiimides.

The carbodiimides are not only effective as stabilizer to inhibit hydrolytic degradation of polyaddition or polycondensation products containing ester groups, or for deacidification of polyesterols which can be used for the preparation of polyester-containing plastics, in particular of polyurethane rubbers, but are also suitable, by way of example, for the termination of esterification reactions during the preparation of polyesters, when the desired degree of polycondensation has been achieved.

The inventive thermoplastically processible polyurethane elastomers may be used for extrusion products, injection-molding products, or calendered products, and also for powder slush processes.

The inventive carbodiimides are preferably used in thermoplastic polyurethanes. The present invention therefore provides processes for the preparation of thermoplastic polyurethane modified with organosilicon groups, in this specification also termed silane-modified thermoplastic polyurethane, i.e. thermoplastic polyurethane having organosilicon groups, and crosslinkable TPUs thus obtainable, in particular cable sheathing, fibers, or hoses, in particular compressed-air hoses, and also the corresponding products crosslinked by way of the silane groups. The invention also provides cable sheathing, fibers, or hoses, in particular compressed-air hoses, based on thermoplastic polyurethane which has been crosslinked by way of silane groups, in particular by way of siloxane groups, in particular cable sheathing, fibers, or hoses in which the crosslinked thermoplastic polyurethane has a Shore A hardness of from 85 to 98 and a Vicat point to DIN EN ISO 306 (10N/120 K/h) above 130° C., particularly preferably above 140° C., in particular above 145° C.

Conventional processes, e.g. injection molding or extrusion, are used to process the TPUs prepared according to the invention, which are usually in the form of granules or powder, to give injection-molded and extruded products, e.g. the desired films, moldings, rollers, fibers, cladding in automobiles, hoses, cable plugs, bellows, drag cables, cable sheathing, gaskets, drive belts, or damping elements. These injection-molding and extrusion products may also be composed of compounded materials comprising the inventive TPU and at least one other thermoplastic, particularly a polyethylene, polypropylene, polyester, polyether, polystyrene, PVC, ABS, ASA, SAN, polyacrylonitrile, EVA, PBT, PET, polyoxymethylene. The TPU prepared according to the invention may in particular be used to produce the products described at the outset.

A preferred method uses the silane-modified thermoplastic polyurethane in well-known processes to spin fibers or to extrude hoses, in particular compressed-air hoses, followed by crosslinking of the thermoplastic polyurethane by way of the silane groups, by means of moisture, if appropriate using a catalyst which accelerates crosslinking. The crosslinking reactions by way of and via the silane groups are familiar to the person skilled in the art and are well known. This crosslinking usually takes place via moisture and can be accelerated via heat or catalysts known for this purpose, e.g. Lewis acids, Lewis bases, Brönsted acids, Brönsted bases. The catalyst to be used for the crosslinking, preferably by means of moisture, is preferably acetic acid, organometallic compounds, such as titanic esters, iron compounds, e.g. ferric acetylacetonate, tin compounds, e.g. stannous diacetate, stannous dioctoate, stannous dilaurate, or the dialkyltin salts of aliphatic carboxylic acids, e.g. dibutyltin diacetate, dibutyltin dilaurate, or the like, particularly preferably stannous dilaurate and/or acetic acid.

EXAMPLES

Example 1

Preparation of Inventive Stabilizers: Isocyanate Stage 1000 parts by weight (4.1 mol) of 1,3-bis(1-methyl-1-isocyanatoethyl)benzene with NCO content of 34.4% by weight were heated to 180° C. in the presence of 2.0 parts by weight of 1-methyl-2-phospholene 1-oxide without solvent and condensed at this temperature with moderate evolution of carbon dioxide. Once the NCO content of the reaction mixture had reached 10% by weight, the reaction time required for this being about 24 hours, the added catalyst and residues of unreacted 1,3-bis(1-methyl-1-isocyanatoethyl)benzene were removed by distillation at a temperature of 190° C. under a pressure of 0.2 mbar.

This gives 730 parts by weight of a mixture composed of mono- and oligomeric polycarbodiimides with an NCO content of 8% by weight, a content of —N=C=N-groups of 15%, a melting point <30° C., and an iodine color number of 4.0, measured to DIN 6162.

$^1$H NMR and IR spectra were used to demonstrate the structure of the mixture having isocyanate groups and composed of mono- and oligomeric polycarbodiimides.

Example 2

Preparation of Inventive Stabilizers: Urea Formation

The product from example 1 was heated to 100° C. 445 g of bis(trimethoxysilylpropyl)amine (Silquest® A-1170 silanes from GE Silicone Osi Specialties) were added dropwise within a period of about 5 h, with vigorous stirring. The reaction mixture was then stirred at 120° C. for a further 2 h.

$^1$H NMR and IR spectra were used to demonstrate the structure of the polycarbodiimide containing methoxysilyl groups.

Example 3

Production of TPU Specimens

Polyol 1)
Polyester polyol BASF Aktiengesellschaft; (butanediol/hexanediol adipate, molecular weight 2000, OH number=56.1)

Polyol 2)
Polyester polyol BASF Aktiengesellschaft; (butanediol/ethylene glycol adipate, molecular weight 2000, OH number=56.1)

The polyols stated in table 1 were mixed at 80° C. with 1,4-butanediol. The various hydrolysis stabilizers listed in table 1 were then added, with stirring.

TABLE 1

| | Experiment | | | |
|---|---|---|---|---|
| | 1 | 2 | 3 | 4 |
| Polyol 1 | 1000 g | 1000 g | 1000 g | 1000 g |
| Butanediol | 110 g | 110 g | 110 g | 110 g |
| Elastostab H01 ® | 8 g | — | — | — |
| Stabaxol 1 ® | — | 8 g | — | — |
| Stabilizer 1 | — | — | 8 g | — |

| | Experiment | | | |
|---|---|---|---|---|
| | 5 | 6 | 7 | 8 |
| Polyol 2 | 1000 g | 1000 g | 1000 g | 1000 g |
| Butanediol | 110 g | 110 g | 110 g | 110 g |
| Elastostab H01 ® | 8 g | — | — | — |
| Stabaxol 1 ® | — | 8 g | — | — |
| Stabilizer 1 | — | — | 8 g | — |

Elastostab ® H01: polymeric carbodiimide (hydrolysis stabilizer) from Elastogran GbmH
Stabaxol ® 1: monomeric carbodiimide (hydrolysis stabilizer) from Rheinchemie GmbH
Stabilizer 1: stabilizer prepared in example 1

The glycol mixture was controlled to 80° G, with stirring. 425 g of 4,4'-MDI (methylenediphenyl diisocyanate) were then added and stirring was continued until the reaction mixture was homogeneous. The mixture was then poured into a flat Teflon dish and annealed at 125° C. for 10 min on a hotplate. The resultant TPU skin was annealed at 100° C. for 24 h in a heated cabinet. The cast sheets were granulated and then processed in an injection-molding machine to give 2 mm injection-molded sheets. The mechanical properties were determined and are listed in table 2.

TABLE 2

| Stabilization method | Shore hardness [A] | Tensile strength [mPas] | Tensile strain at break [%] | Tear propagation resistance [N/mm] | Abrasion [mm³] | Density [g/cm³] |
|---|---|---|---|---|---|---|
| Experiment 1 | 82 | 49 | 580 | 65 | 35 | 1.183 |
| Experiment 2 | 82 | 52 | 600 | 68 | 34 | 1.183 |
| Experiment 3 | 83 | 47 | 590 | 69 | 35 | 1.182 |
| Experiment 4 | 84 | 44 | 630 | 75 | 33 | 1.185 |
| Experiment 5 | 84 | 47 | 700 | 67 | 36 | 1.218 |
| Experiment 6 | 85 | 50 | 700 | 73 | 41 | 1.218 |
| Experiment 7 | 84 | 49 | 680 | 71 | 40 | 1.220 |
| Experiment 8 | 85 | 47 | 620 | 70 | 38 | 1.225 |

TABLE 3

| Properties | Unit | DIN | ISO |
|---|---|---|---|
| Hardness | Shore A | 53505 | 868 |
| Density | kg/m³ | 53479 | 1183 |
| Tensile strength | MPa | 53504 | 37 |
| Tensile strain at break | % | 53504 | 37 |
| Tear propagation resistance | N/mm | 53515 | 34 |
| Abrasion | mm³ | 53516 | 4649 |

Determination of Resistance to Hydrolysis

S2 test specimens were stamped out from the injection-molded sheets, and these were placed in glass containers (250 and 500 ml) with distilled water and placed in a temperature-controlled cabinet at a defined temperature (80° C.). At certain intervals (e.g. weekly) 3 test specimens were removed. The specimens were then aged in standard 23/50 conditions of temperature and humidity for not less than 30 minutes, and tensile strength and tensile strain at break were determined.

TABLE 4

Measurement of tensile strength [MPa] as a function of time [days]

| Expired time [d] | Experiment 1 | Experiment 2 | Experiment 3 | Experiment 4 |
|---|---|---|---|---|
| 0 | 49 | 52 | 47 | 44 |
| 7 | 44 | 44 | 44 | 25 |
| 14 | 45 | 46 | 45 | 7 |
| 21 | 44 | 44 | 44 | Disintegrated |
| 28 | 43 | 43 | 44 | |
| 35 | 42 | 40 | 43 | |
| 42 | 42 | 38 | 43 | |
| 49 | 42 | 40 | 43 | |
| 56 | 42 | 33 | 42 | |
| 63 | 40 | 17 | 42 | |
| 70 | 41 | 4.75 | 41 | |
| 77 | 36 | 2 | 42 | |
| 84 | 24 | Disintegrated | 40 | |
| 91 | 6 | | 37 | |
| 98 | Disintegrated | | 33 | |
| 105 | | | 18 | |
| 112 | | | 2 | |

TABLE 5

Measurement of tensile strain at break [%] as a function of time [days]

| Expired time [d] | Experiment 1 | Experiment 2 | Experiment 3 | Experiment 4 |
|---|---|---|---|---|
| 0 | 580 | 600 | 590 | 630 |
| 7 | 520 | 560 | 550 | 770 |
| 14 | 550 | 570 | 580 | 530 |
| 21 | 540 | 580 | 590 | Disintegrated |
| 28 | 550 | 600 | 590 | |
| 35 | 540 | 580 | 600 | |
| 42 | 620 | 650 | 590 | |
| 49 | 590 | 650 | 610 | |
| 56 | 620 | 730 | 610 | |
| 63 | 590 | 780 | 620 | |
| 70 | 610 | 275 | 610 | |
| 77 | 610 | 40 | 610 | |
| 84 | 750 | Disintegrated | 600 | |
| 91 | 450 | | 650 | |
| 98 | Disintegrated | | 800 | |
| 105 | | | 350 | |
| 112 | | | 80 | |

TABLE 6

Measurement of tensile strength [MPa] as a function of time [days]

| Expired time [d] | Experiment 5 | Experiment 6 | Experiment 7 | Experiment 8 |
|---|---|---|---|---|
| 0 | 47 | 50 | 49 | 47 |
| 7 | 42 | 41 | 45 | 27 |
| 14 | — | — | — | 6 |
| 21 | 39 | 36 | 41 | Disintegrated |
| 28 | 35 | 32 | 38 | |
| 35 | 27 | 16 | 33 | |
| 42 | 7 | 4 | 31 | |
| 49 | Disintegrated | Disintegrated | 25 | |
| 56 | | | 3 | |
| 63 | | | Disintegrated | |
| 70 | | | | |

TABLE 7

Measurement of tensile strain at break [%] as a function of time [days]

| Expired time [d] | Experiment 5 | Experiment 6 | Experiment 7 | Experiment 8 |
|---|---|---|---|---|
| 0 | 700 | 700 | 680 | 620 |
| 7 | 640 | 660 | 650 | 770 |
| 14 | — | — | — | 420 |
| 21 | 690 | 700 | 710 | Disintegrated |
| 28 | 680 | 780 | 730 | |
| 35 | 840 | 900 | 750 | |
| 42 | 580 | 280 | 810 | |

TABLE 7-continued

Measurement of tensile strain at break [%] as a function of time [days]

| Expired time [d] | Experiment 5 | Experiment 6 | Experiment 7 | Experiment 8 |
|---|---|---|---|---|
| 49 | Disintegrated | Disintegrated | 950 | |
| 56 | | | 250 | |
| 63 | | | Disintegrated | |
| 70 | | | | |

The invention claimed is:

1. A carbodiimide containing the following structure:

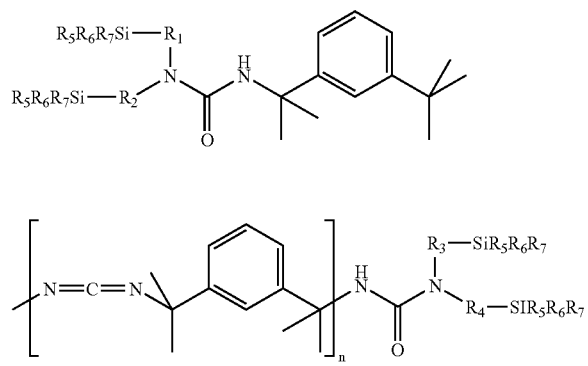

with the following meanings for n, $R_1$, $R_2$, $R_3$ $R_4$, $R_5$, $R_6$ and $R_7$:

n: 1, 2, 3, 4, 5, 6, 7, 8, 9, 10, 11, 12, 13, 14, 15, 16, 17, 18, 19, or 20, $R_1$: aliphatic, cycloaliphatic, araliphatic, or aromatic, if appropriate substituted, if appropriate branched-chain radical, $R_2$: aliphatic, cycloaliphatic, araliphatic, or aromatic, if appropriate substituted, if appropriate branched-chain radical, $R_3$: aliphatic, cycloaliphatic, araliphatic, or aromatic, if appropriate substituted, if appropriate branched-chain radical, $R_4$: aliphatic, cycloaliphatic, araliphatic, or aromatic, if appropriate substituted, if appropriate branched-chain radical, $R_5$: methyl-, ethyl, —O—$CH_3$, —O—$CH_2$—$CH_3$, —O—CH($CH_3$)$_2$, —O—C($CH_3$)$_3$, or —O—$CH_2$—$CH_2$—O—$CH_3$ $R_6$: methyl-, ethyl, —O—$CH_3$, —O—$CH_2$—$CH_3$, —O—CH($CH_3$)$_2$, —O—C($CH_3$)$_3$, or —O—$CH_2$—$CH_2$—O—$CH_3$ $R_7$: methyl-, ethyl, —O—$CH_3$, —O—$CH_2$—$CH_3$, —O—CH($CH_3$)$_2$, —O—C($CH_3$)$_3$, or —O—$CH_2$—$CH_2$—O—$CH_3$.

2. A mixture comprising carbodiimides according to claim 1 and at least one compound selected from the group consisting of: polyurethanes which have ester structures, polyethylene terephthalate and/or polybutylene terephthalate, polyetheresters, polyesteramides, polycaprolactones, unsaturated polyester resins, and polyamides.

3. A thermoplastic polyurethane comprising the carbodiimide according to claim 1 and optionally ester structures.

4. A process for the preparation of the carbodiimide of claim 1, which comprises reacting 1,3-bis(1-methyl-1-isocyanatoethyl)benzene in the presence of catalysts with elimination of carbon dioxide to give carbodiimides, and then reacting the carbodiimide having isocyanate groups with a secondary amine containing at least one silane group.

5. A process for the preparation of the carbodiimide of claim 1, which comprises reacting 1,3-bis(1-methyl-1-isocyanatoethyl)benzene with a submolar amount of secondary amine containing at least one silane group, and then reacting the reaction product having isocyanate groups in the presence of catalysts with liberation of carbon dioxide to give carbodiimides.

6. A process for the preparation of polyurethanes, which is carried out in the presence of carbodiimides according to claim 1.

7. A carbodiimide containing the following structure:

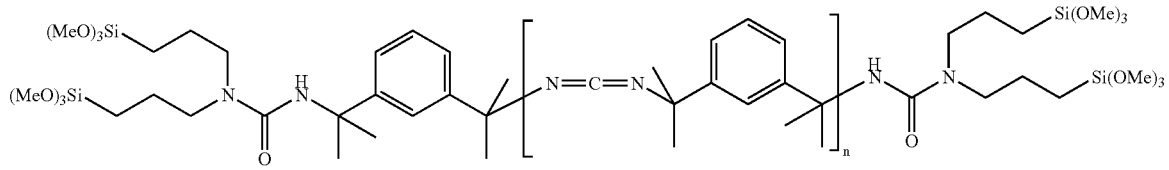

with the following meaning for n: 1, 2, 3, 4, 5, 6, 7, 8, 9, 10, 11, 12, 13, 14, 15, 16, 17, 18, 19 or 20.

8. A mixture comprising carbodiimides according to claim 7 and at least one compound selected from the group consisting of: polyurethanes which have ester structures, polyethylene terephthalate and/or polybutylene terephthalate, polyetheresters, polyesteramides, polycaprolactones, unsaturated polyester resins, and polyamides.

9. A thermoplastic polyurethane comprising the carbodiimide according to claim 7 and optionally ester structures.

10. A process for the preparation of polyurethanes, which is carried out in the presence of carbodiimides according to claim 7.

* * * * *